(12) United States Patent
Verin et al.

(10) Patent No.: US 8,048,072 B2
(45) Date of Patent: Nov. 1, 2011

(54) MEDICAL DEVICE FOR TISSUE ABLATION

(75) Inventors: Vitali Verin, Geneva (CH); Jan Sandtner, Oberdorf (CH)

(73) Assignee: Les Hospitaux Universitaires de Geneva (CH)

( * ) Notice: Subject to any disclaimer, the term of this patent is extended or adjusted under 35 U.S.C. 154(b) by 191 days.

(21) Appl. No.: 12/373,281

(22) PCT Filed: Jul. 6, 2007

(86) PCT No.: PCT/IB2007/001869
§ 371 (c)(1),
(2), (4) Date: Jan. 9, 2009

(87) PCT Pub. No.: WO2008/010039
PCT Pub. Date: Jan. 24, 2008

(65) Prior Publication Data
US 2010/0004661 A1    Jan. 7, 2010

(30) Foreign Application Priority Data
Jul. 12, 2006 (WO) .................. PCT/IB2006/001917

(51) Int. Cl.
*A61B 18/14* (2006.01)
(52) U.S. Cl. .............................. 606/41; 606/34; 607/102
(58) Field of Classification Search .............. 606/32–50; 607/101–105, 115–116
See application file for complete search history.

(56) References Cited

U.S. PATENT DOCUMENTS

| | | | |
|---|---|---|---|
| 5,429,131 A | 7/1995 | Scheinman et al. | |
| 6,807,968 B2* | 10/2004 | Francischelli et al. | 128/898 |
| 2005/0187545 A1 | 8/2005 | Hooven et al. | |
| 2005/0267571 A1* | 12/2005 | Spence et al. | 623/2.11 |
| 2006/0069385 A1 | 3/2006 | Lafontaine et al. | |
| 2006/0106375 A1 | 5/2006 | Werneth et al. | |

FOREIGN PATENT DOCUMENTS

| | | |
|---|---|---|
| EP | 1591058 A1 | 11/2005 |
| WO | 00/69353 A1 | 11/2000 |
| WO | 01/05306 A1 | 1/2001 |

OTHER PUBLICATIONS

International Search Report, PCT/IB2007/001869, dated Jan. 31, 2008.

* cited by examiner

*Primary Examiner* — Michael Peffley
*Assistant Examiner* — Daniel Fowler
(74) *Attorney, Agent, or Firm* — Sheridan Ross P.C.

(57) ABSTRACT

A medical device for ablating tissues within a heart chamber comprising a guiding member intended to be introduced in the oesophagus of the patient and an ablating member comprising an ablation electrode mounted at the distal end or tip of catheter. Both the head of the guiding member and the tip of the ablating member are magnetised and can enter into magnetic coupling when their distal ends are brought in close contact. Once the magnetic coupling is achieved, the tip of the ablating member is guided by moving the guiding member. The guiding member can include sensors enabling to monitor physiological parameters during the intervention.

18 Claims, 10 Drawing Sheets

Fig. 1
Fig. 2
Fig. 3
Fig. 4
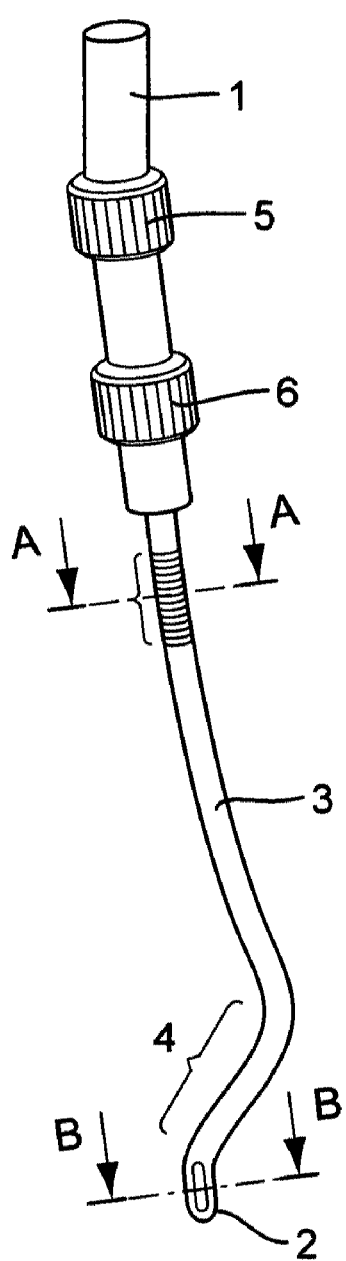
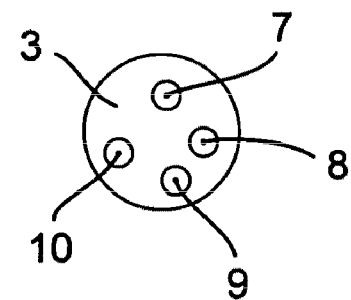
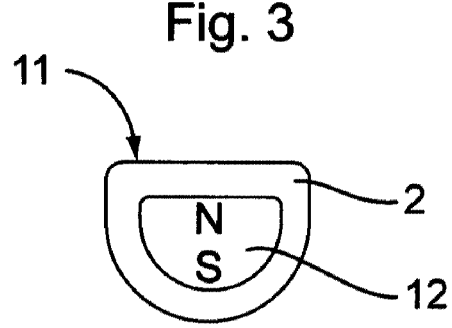
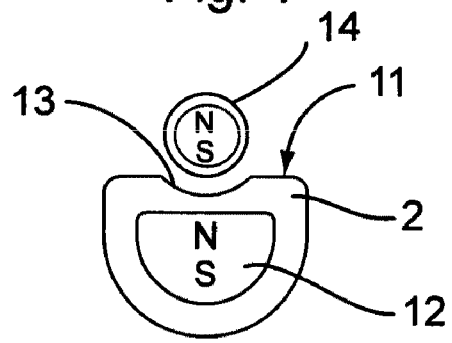

MEDICAL DEVICE FOR TISSUE ABLATION

CROSS REFERENCE TO RELATED APPLICATIONS OR PRIORITY CLAIM

This application is a national phase of International Application No. PCT/IB2007/001869, entitled "MEDICAL DEVICE FOR TISSUE ABLATION", which was filed on Jul. 6, 2007, and which claims priority of International Application No. PCT/IB2006/001917, filed Jul. 12, 2006.

DESCRIPTION

The present invention relates to an improved medical device or apparatus for ablating cardiac tissues along continuous lines in the heart chambers. A further object of the invention relates to a method for positioning and guiding an ablation catheter during ablation procedure. More particularly the device and method of the present invention are intended to perform ablation lines on the posterior wall of the left atrium in order to treat and prevent the occurrences of atrial fibrillation. The medical device comprises to that extent an elongated member having a distal end comprising an ablation electrode and a second elongated member or guiding member allowing precise control of the ablation electrode.

Abnormal heart rhythms are generally referred to as cardiac arrhythmias and with an abnormally rapid rhythm called tachycardia. Atrial fibrillation is an abnormal rhythm of the heart caused by abnormal electrical discharges within the two upper chambers of the heart called atria. Atrial fibrillation reduces the ability of the atria to pump blood into the lower chambers of the heart (the ventricles) and usually causes the heart to beat too rapidly and may induce complications that include heart failure and stroke.

While medication has been used to prevent recurrence of atrial fibrillations, they are not always effective and may induce undesirable or intolerable side effects. Furthermore they do not cure the underlying causes. Implantable devices have also been used but they only correct the arrhythmia after it occurs and do not help to prevent it.

Surgical and invasive catheterisation approaches in contrast are promising and give very good results as they cure the problem by ablating the portion of the heart tissue that causes electrical trouble inducing fibrillation.

Before performing ablation of some portion of the inner wall of atria, a cardiac mapping is firstly executed in order to locate aberrant electrical pathways within the heart as well as to detect other mechanical aspects of cardiac activity. Various methods and devices have been disclosed and are commonly used to establish precise mapping of the heart and will not be further described in the present application. Once this mapping is done, the clinician will refer to this heart mapping, which indicates him the points and lines along, which ablation is to be performed.

One commonly used technique for performing ablation is known as radiofrequency catheter ablation. This technique uses an ablation electrode mounted at the distal end of a catheter that is introduced by natural passageways in the target heart chamber and then manipulated by a surgeon thanks to a handle at the proximal end of the catheter acting on a steering mechanism. This allows displacement of the distal end of the catheter so as to have the ablation electrode lying at the exact position determined by the heart mapping technique or/and fluoroscopy. Once the ablation electrode is in contact with the pre-determined area, RF energy is applied to ablate the cardiac tissue. By successfully causing a lesion on the pre-determined portion of the cardiac tissues, the abnormal electrical patterns responsible of the atrial fibrillation are eliminated.

However, this technique presents several difficulties. The currently used techniques of manual catheter ablation as well as robotic ablation systems in development do not allow precise controlled movements of the ablation electrode tip along the internal atrial wall surface. The ablation electrode located at the distal end of the catheter tends to slip and jump from one point to another instead of following a straight line. The absence of real time visualisation of the atrial wall during the intervention hampers the generation of precise continuous ablation lines. The gaps between ablation points are commonly leading to a lack of efficiency and may induce development of atrial flutter.

Another known problem relates to the determination of the correct level of energy to deliver to the ablation tip so as to precisely control the ablation lesion depth. When the catheter distal end is not correctly positioned or when the ablation electrode is not perpendicular to the cardiac tissue, energy applied may be either too low, in that case the lesion is ineffective, or too high which may lead in rare case to oesophageal burns and atrial-oesophageal fistula formation. This complication, although rare, is extremely devastating and fatal in more that a half of the reported cases.

The use of a temperature sensor at the tip of the catheter in the vicinity of the ablating electrode does not help to solve this problem as it does not provide an accurate measure of the tissue temperature because the measure is mostly influenced by the heating of the ablation electrode when RF energy is applied.

The goal of the present invention is to provide a medical device or apparatus and a method that allows the precise control of the positioning and of the movements of the ablation electrode during the intervention and to effectively monitor the adequate physiological parameters to prevent or even eliminate the occurrence of the above-mentioned dreadful complication.

This goal is achieved thanks to a medical apparatus encompassing the characteristics recited in claim 1 and a method for guiding an ablation electrode during an ablation intervention of some portion of a heart chamber wall as recited in claim 9.

Other characteristics of the medical apparatus and of the method object of the present invention are recited in the dependant claims.

The details of one or more embodiments of the invention are set forth in the accompanying drawings and the description below. Other features, objects and advantages of the invention will be apparent from the following detailed description and drawings in which:

FIG. 1 is a schematic representation of a guiding member intended to guide the ablation catheter.

FIG. 2 is a cross-sectional view taken along line A-A of FIG. 1.

FIG. 3 is a cross-sectional view taken along line B-B of FIG. 1.

FIG. 4 is a cross-sectional view taken along line B-B of FIG. 1 representing and alternate embodiment of the guiding member head.

Figure 5:
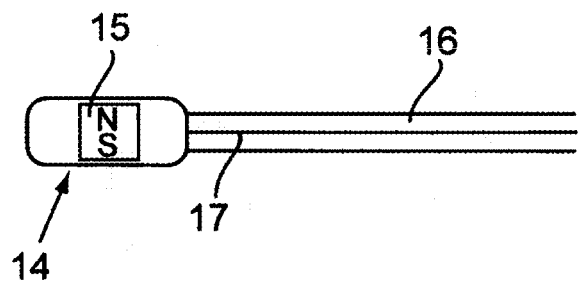
FIG. 5 is schematic representation of the tip of the ablating member of the medical device.

Generally, the medical device object of the present invention comprises two different elongated members having distal and proximal ends intended to be introduced in the human body by natural passageways thanks to known techniques like catheterisation for example. Both distal ends of the two members comprise a magnet or a magnet arrangement and can therefore be magnetically coupled when they are brought in close together. It is to be noted that each member is intended to be introduced in a different cavity of the human body therefore magnetic coupling between the distal ends of the two members always occurs through the wall of internal organs. By way of example, one of the members can be introduced into one heart chamber and the second or guiding member in the oesophagus of the patient. Other combinations are of course possible, as it will be disclosed later. The distal end of one member comprises, in addition to the magnet or magnet arrangement, means for ablating human tissues. The distal end of the second member includes a temperature sensor that monitors the temperature of the opposite side of the tissue being ablated when both distal ends are magnetically coupled. Preferably, at least one of the two members will comprise means for moving its distal end in various directions. Such means are by way of example wires extending from the proximal end to the distal end and connected to a steering mechanism that can be actuated by a handle located at the proximal end like in traditional biomedical catheters. In a further embodiment, the distal ends of both members may be manipulated independently by appropriate means. In the following disclosure, the medical device according to the invention will be described in relation to a preferred embodiment in connection with the ablation of some portion of the inner wall of the left atrium. Obviously there may be many other interventions that can be performed according to the same principle without departing from the spirit of the invention.

Anatomic observations have shown that the oesophagus is in contact with the left atrium external wall at the level of the superior border of the posterior left atrium and remains in contact beyond the level of the inferior pulmonary veins. It is thus one of the objects of the invention to guide an ablation catheter located in the heart chamber thanks to a guiding member that is introduced in the oesophagus of the patient and then coupled thanks to magnetic attraction through the wall of the oesophagus and the wall of the atrium, to the ablation electrode located in the atrium. To that extent, the medical apparatus object of the present invention comprises two different elongated members.

A first or ablating member comprising at its distal end an ablation mean as for example an electrode connected to an RF generator adapted to perform tissues ablation in the atria. A second member or guiding member consists of a catheter tube intended to be introduced in the oesophagus of the patient through the mouth or the nose and guided within the portion of the oesophagus lying in the vicinity of the left atrium. The distal end of both members comprises at least a magnet or a magnet arrangement that allows the magnetic coupling through both the oesophagus and the atrium walls, of the distal ends of both members when they come close together. Once the magnetic coupling is achieved, the guiding member in the oesophagus of the patient can be used to guide the ablation member along a predetermined trajectory to ablate cardiac tissues.

With reference to FIG. 1, the guiding member intended to be introduced in the oesophagus of a human body comprises a handle 1 located at the proximal end and a distal end further referenced as the head 2. A flexible hollow plastic tube 3 connects proximal and distal ends. The lower portion 4 of the tube 3 is made of a flexible plastic material and incorporates the distal end or head 2 of the guiding member. The handle 1 of this member further comprises a steering mechanism with two rotating command buttons, 6 allowing the lower portion of the catheter tube 4 and hence of the head 2 to be moved and displaced in various directions. The upper section of the catheter tube 3 has equidistant markers used to visually appreciate the length of advancement/withdrawal of the catheter into/from the oesophagus of the patient and hence the longitudinal displacement of the distal head 2 within the oesophagus of the patient.

FIG. 2 is a cross sectional view taken along line A-A of FIG. 1 and shows four wires 7,8,9,10, connected to the command buttons, 6 and extending down to the catheter head 2. These wires actuated thanks to the rotation of the command buttons, 6 allow transmitting tension to the flexible section 4 and permit the flexion of the catheter head 2 in different planes.

The distal end or catheter head 2 of the guiding member comprises a magnetised portion having at least one permanent magnet or an arrangement of permanent magnets that will be described later.

FIG. 3 is a cross sectional view of the oesophageal catheter head 2 taken along line B-B of FIG. 1 and shows the north (N) and south (S) poles of the permanent magnet 12. The permanent magnet 12 is fully incorporated in the plastic head 2 at the distal end of the catheter tube 3 therefore providing an electrical isolation of the catheter head 2. As it will be seen in the following paragraphs, the magnetised distal head 2 of the guiding member is intended to be coupled and to cooperate with a corresponding magnetised end of an ablation member and therefore in case RF energy is used for ablation it is important that the head 2 of the guiding member is electrically isolated. The absence of isolation in this case could cause the generation of capacitive currents leading to an unwanted heating of the guiding member head 2 with the risk of thermal injury to the oesophageal wall. The guiding member head 2 is preferably shaped in such a manner as to present at least one flat surface 11 intended to be positioned against the inner wall of the oesophagus during the intervention. An alternative configuration of the guiding member head 2 is illustrated at FIG. 4 and presents a hemi-cylindrical recess 13 located within the flat surface 11 allowing a better docking of the cylindrical ablation tip that will be described later.

The medical device object of the present invention comprises a fits or ablating member for performing ablation constituted as an example of at least one conventional ablation electrode mounted at the distal end of a catheter having a proximal and a distal ends as well as a lumen extending between the two extremities. A radio frequency (RF) ablation probe containing at least one ablation electrode is located at the extremity of the distal end of the ablation member and if needed may be manipulated by a physician by actuating the handle located at the proximal end or by movement of an external sheath or by bended internal core wire. The working principle of such ablation catheter devices are well known in the art and will not be further described in detail in the present application. Both monopolar and bipolar ablation catheter may be used in the present invention.

Figure shows schematically the distal end of the ablating member that will be further referenced as the tip 14 of the ablating member. The tip 14 incorporates a permanent magnet 1 in which the north and south poles are referenced with the corresponding (N) and (S) letters. The shape of the tip 14 of the ablation member is generally cylindrical but may take other shapes and incorporates both a permanent magnet 1 and a conventional ablation electrode. The tip 14 of the ablation member is attached to a flexible plastic tube 16 and a conductive wire 17 allows the delivery of an electrical current to the ablation electrode. In a variant the tip 14 and the distal part of the tube 16 could incorporate more than one ablation or/and sensing electrodes.

Figure 6:
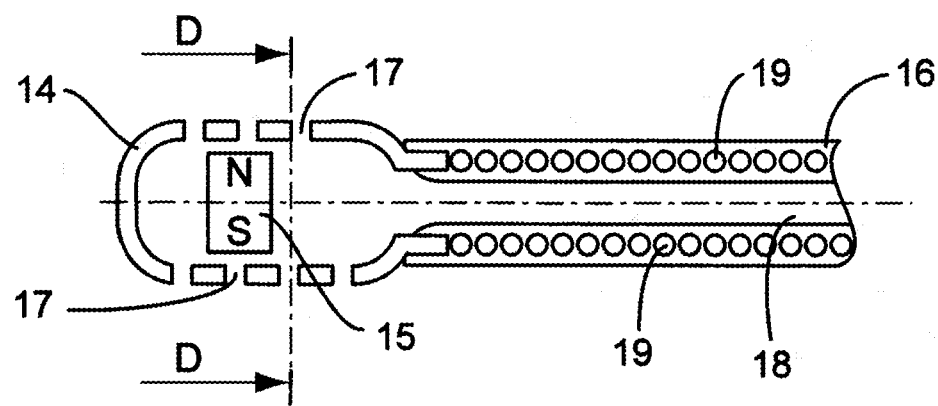
FIG. 6 is a cross-sectional view of an alternate embodiment of the distal end of the ablating member.
Figure 7:
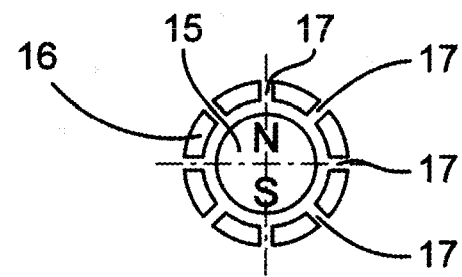
FIG. 7 is a cross-sectional view taken along line D-D of FIG. 6.

FIG. 6 shows a variant of the ablation member tip 14, which also comprises a magnet, preferably a permanent magnet 1, located within the cylindrical tip 14 of the catheter. The cylindrical tip 14 is affixed to the flexible tube 16 and presents a multitude of irrigation holes 17. Water can be injected through the lumen 18 of the plastic tube 16 from the proximal end to the tip 14 for cooling and cleaning purposes. In this embodiment, electric current is delivered to the ablation electrode within the tip 14 through coiled metallic wires 18 incorporated within the flexible plastic tube 16. In this configuration, the coiled electric wires 19 also have a maintaining function and prevent the collapse of the lumen 18 within the catheter.

Figure 8:
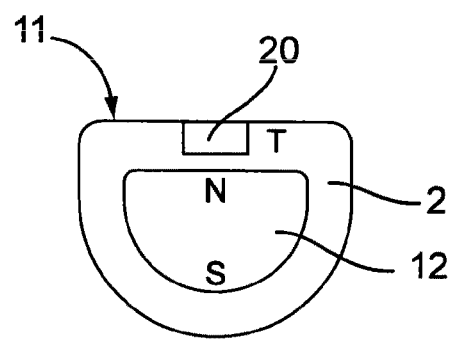
FIG. 8 is a cross-sectional view similar to FIG. 3 but showing an alternate embodiment of the distal head of the guiding member.

In a preferred embodiment of the distal end of the guiding member shown at FIG. 8, the head 2 of the guiding member comprises a temperature sensor 20 allowing a precise measure of the temperature at the point of contact of the flat surface 11 of the head 2 onto the oesophagus wall. The temperature sensor 20 may be of any known type like for example, a thermocouple, a thermistor or other known means for measuring the temperature like optical fibre based sensors.

Figure 9:
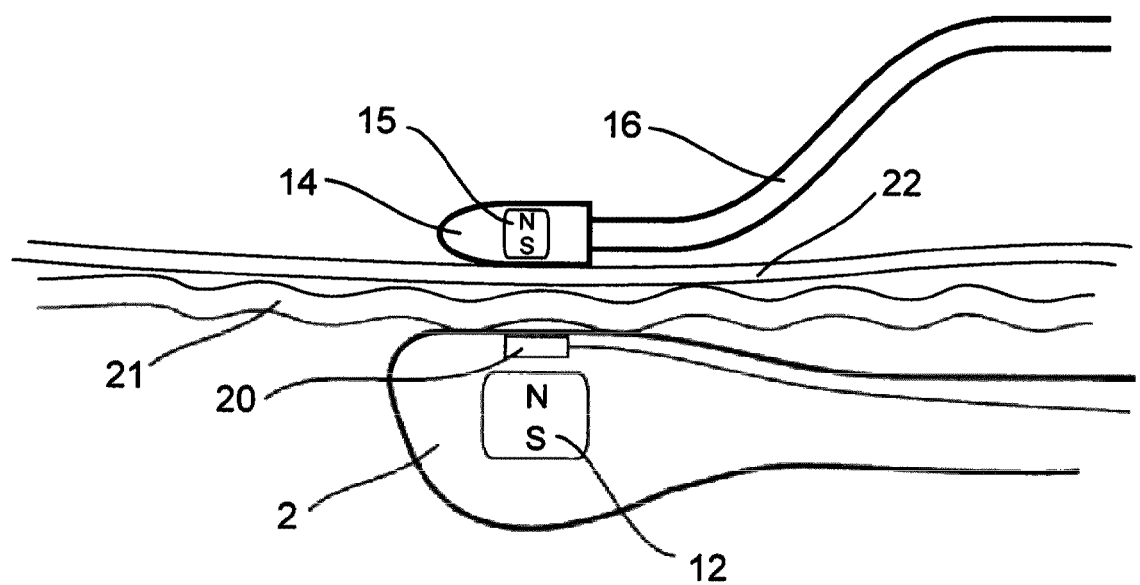
FIG. 9 is a schematic view of the guiding member magnetically coupled to the ablating member.

FIG. 9 as an example of the preferred embodiment shows the guiding member head 2 in contact with the inner wall 21 of the oesophagus as well as the ablation tip 14 lying against the inner wall 22 of the atrium where the head 2 and the tip 14 are magnetically coupled. Thanks to the temperature sensor 20, the clinician may monitor the temperature at the point of contact of the inner oesophageal wall 21 and adjust the energy delivered to the ablation electrode in the ablation member tip 14 so as to prevent burning of the oesophagus wall. Energy delivered to the ablating electrode can be adjusted manually by the clinician in response to the temperature measures but the process of delivering the adequate level of energy to the ablation electrode could also be automated with an electronic control of the RF generator controlled by the temperature sensor.

Traditional ablating catheters incorporate a temperature sensor located in the ablation tip, however these devices do not allow direct measurement of the temperature of the tissue at the point of ablation but instead provide a measure of the temperature of the catheter tip itself. This measure is not relevant as it is not indicative of the temperature of the tissue itself but is mostly influenced either by the heating of the ablation electrode when energy is delivered to the ablation tip or by the cooling process when a cooling fluid is supplied to the ablation tip. By placing the temperature sensor 20 in the head 2 of the guiding member instead of within the ablation tip 14, a much more precise measure of the temperature of the tissues (either the inner part of the oesophageal wall 21 of the surface of the atrial wall 22) is achieved, thus preventing fatal lesions due to overheating during the ablation process. By continuously monitoring the temperature thanks to the temperature sensor 20, it is possible to ablate tissues in a continuous movement of the catheters and therefore to produce continuous lines of ablation instead of discrete point-by-point movements.

Figure 10:
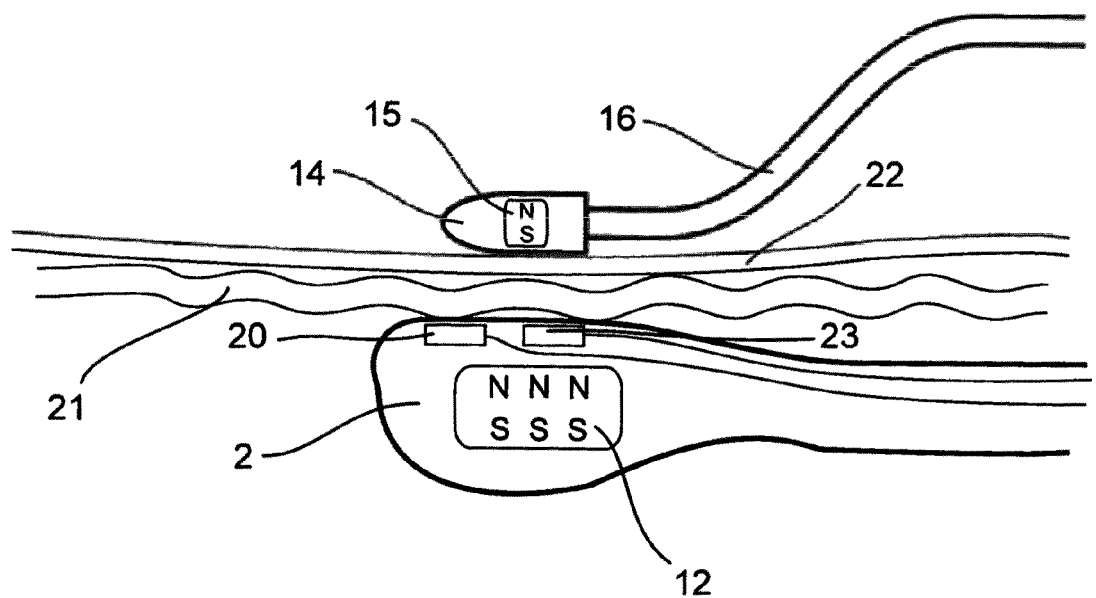
FIG. 10 is a view similar to the one depicted at FIG. 9 showing a variant of the distal end of the guiding member.

In a further preferred embodiment of the guiding member as shown at FIG. 10, the side of the head 2 intended to contact the inner oesophageal surface comprises a force/pressure sensor 23 located in the vicinity of the temperature sensor 20 between the outer surface of the head 2 and the magnet 1. The function of this pressure sensor 23 is to provide a precise indication of the tissues compression between the two magnets. It allows measuring the force created on the tissues by the interaction of the two magnets 12,1. Knowing this parameter, the clinician will also be warned if the oesophageal head 2 is wrongly positioned against the oesophageal wall.

Figure 11:
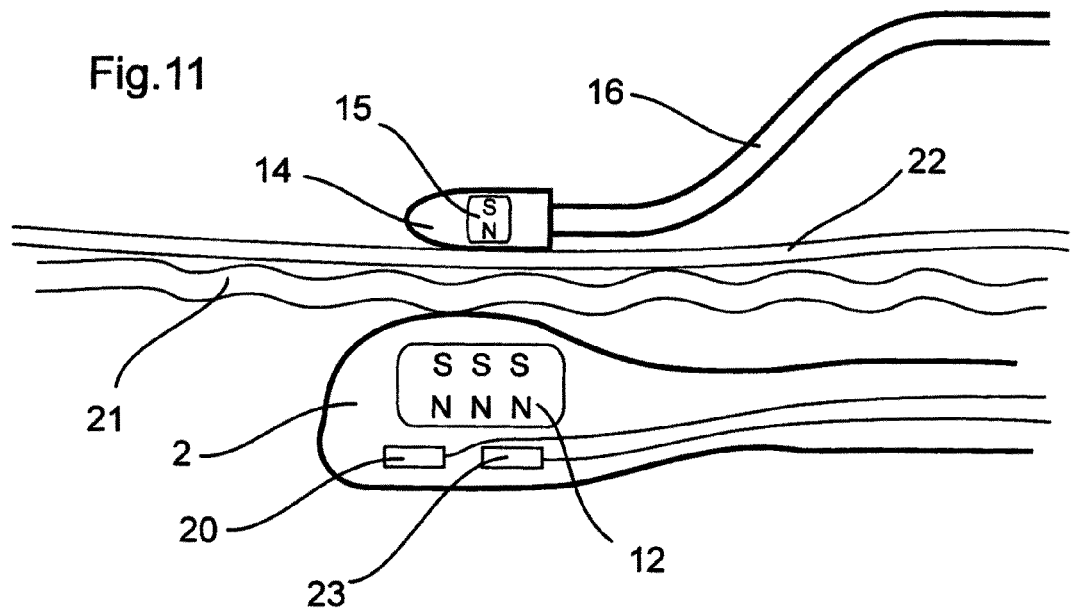
FIG. 11 is a view similar to FIGS. 9 and 10 in which the guiding member head and the ablating tip are magnetically coupled in reverse position.

If by way of example the round surface of the head 2 is in contact with the inner oesophageal wall, instead of the flat surface 11, the magnetic connection could still occur with the ablation tip 14 upside down as shown at FIG. 11. In this case the pressure sensor will deliver a value which is not within the normal range knowing the parameters of the magnets and giving that way an indication to the clinician that the head 2 and the ablation tip 14 are connected in the opposite direction. A further advantage of including a pressure sensor is that knowing the force of interaction between the two magnets, it will allow the calculation of the distance between the head 2 of the guiding member and the tip 14 of the ablating member. Knowing such distance in connection with the temperature measure of the inner wall of the oesophagus will allow to improve the algorithm for calculating with high accuracy the level of energy to apply to the ablating electrode and therefore allows a more precise diameter and deepness of the ablation lesion to be created on the internal wall of the atria.

The force/pressure sensor could be arranged in such a way that it measures only the force produced by the displacement of the magnet 12 towards the magnet 1 and do not measure the force resulting from the contact between the head 2 and the surface of the tissue. To that extent, the magnets are mounted resiliently, for example with springs, within the rigid casing of the head 2. The magnet 12 is therefore free to move in the vertical direction within the casing of the head 2. At the rest position the magnet 12 is centred within the casing of the head 2 and do not enter into contact with the force/pressure sensor. Once magnetic coupling occurs, the magnet is displaced against the force/pressure sensor. This will allow measuring of only the force of interaction between two magnets. As this force is dependent only on the distance between the two magnets, a precise measure of the distance between the head 2 and the tip 14 can be achieved. Knowing such distance as well as the temperature of the oesophageal wall allows optimizing the algorithm of calculation of the temperature of the atrial surface based on measured temperature on the oesophageal wall.

Figure 12:
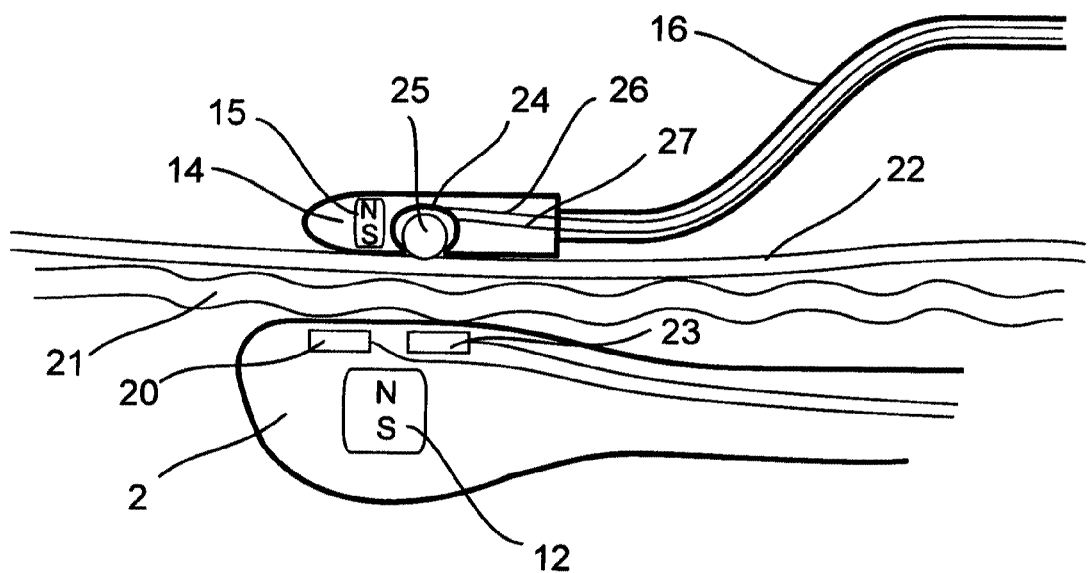
FIG. 12 is a view of a further embodiment of the distal tip of the ablating member comprising means for calculating displacement distances.

With reference to FIG. 12, an alternate embodiment of the ablation member tip is illustrated. The ablation tip 14 comprises a spherical recess 24 in which a ball 2 can freely rotate when driven along the wall of the atria. Furthermore, two optical fibres 26,27 are arranged in the tip 14 in such a way that they can deliver a signal corresponding to the rotation of the ball 2 thus allowing determining the distance covered by the tip 14 when moving along the surface of the atrial wall.

Figure 13:
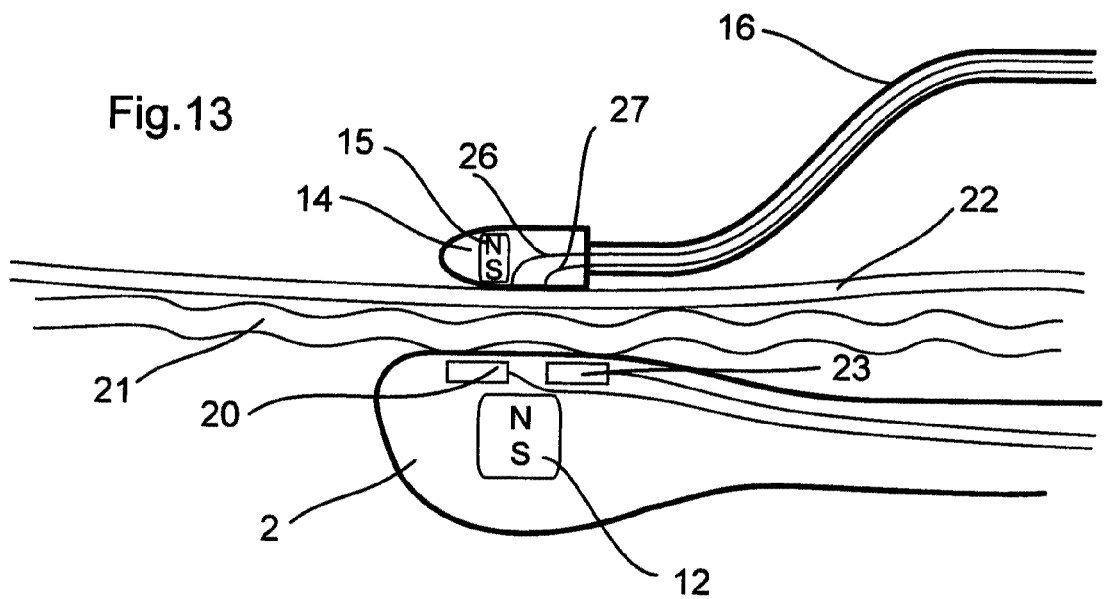
FIG. 13 is a view of a further embodiment of the distal tip of the ablating member comprising alternate means for calculating displacement distances.

FIG. 13 shows an alternate embodiment that also allows determining the displacement of the ablating tip 14 over the atrial wall. In this embodiment there is no rotating ball but instead two optical fibres that read directly the displacement of the tip 14 relative to the atrial wall.

Figure 14:
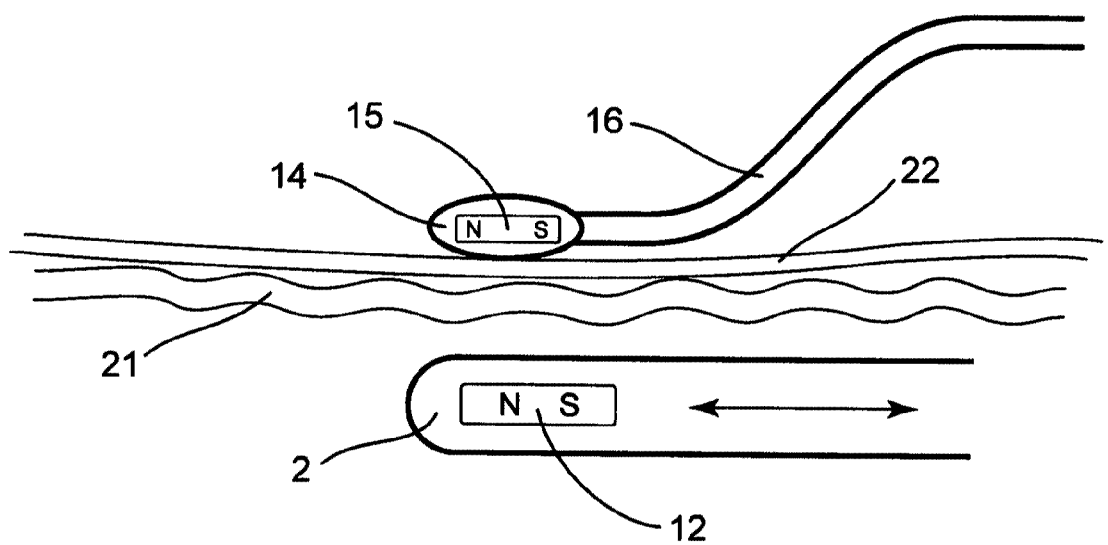
FIG. 14 shows a further embodiment of the distal tip of the ablating member and of the guiding member.
Figure 15:
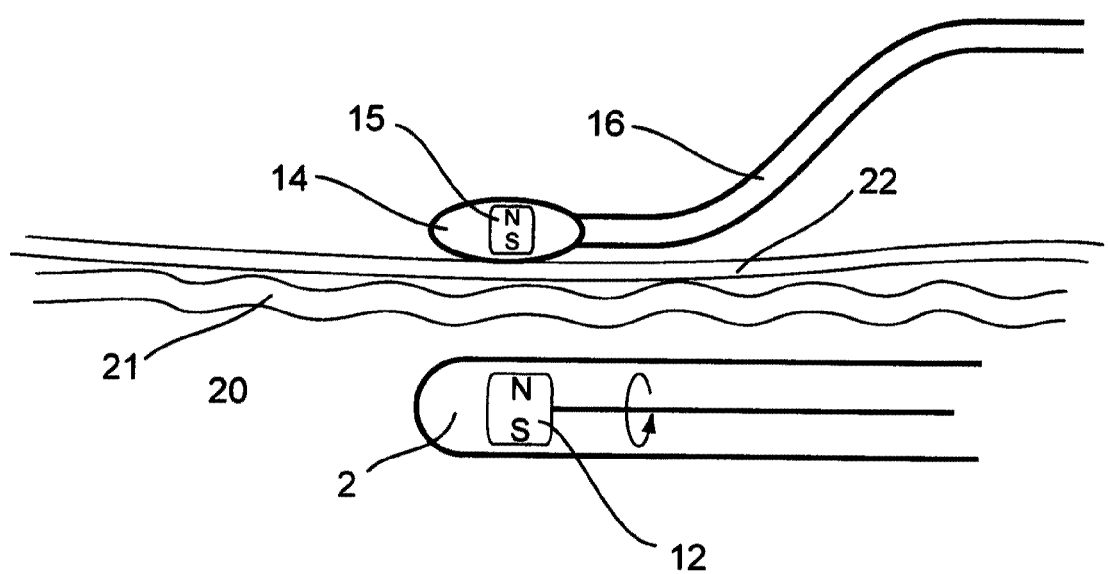
FIG. 15 shows another further embodiment of the distal tip of the ablating member.

FIG. 14 shows another alternate embodiment of the ablating tip 14 in which the shape of the ablating tip 14 is an ovoid. This shape allows smoother displacement of the ablating tip 14 on the surface of the heart chamber by minimizing the contact zone between the ablating tip 14 and the surface 22 of the heart chamber. As the surface of the heart chambers are not perfectly flat but may present irregularities and/or obstacles, the ovoid shape is preferred as it allows easier displacement of the ablating tip. The magnet 1 in the ablating tip 14 is placed longitudinally as opposed to the previous embodiments in which the north and south poles were arranged vertically. The corresponding magnet in the guiding member 2 is accordingly also arranged longitudinally. Both arrangement, vertical and longitudinal can be used indifferently. Clinical tests have shown that even when an ovoidally shaped ablating tip 14 was used the ablating tip was sometimes magnetically disengaged with the guiding member 2, because it encounters an obstacle. In order to improve the magnetic connection and therefore the guiding of the ablating tip 14, it was experimented to induce a movement to the guiding member to improve the guiding process of the ablating tip. This movement can be longitudinal as depicted by the arrow at FIG. 14 in which a back and forth movement is applied to the guiding member or rotational as illustrated schematically at FIG. 1.

Figure 16:
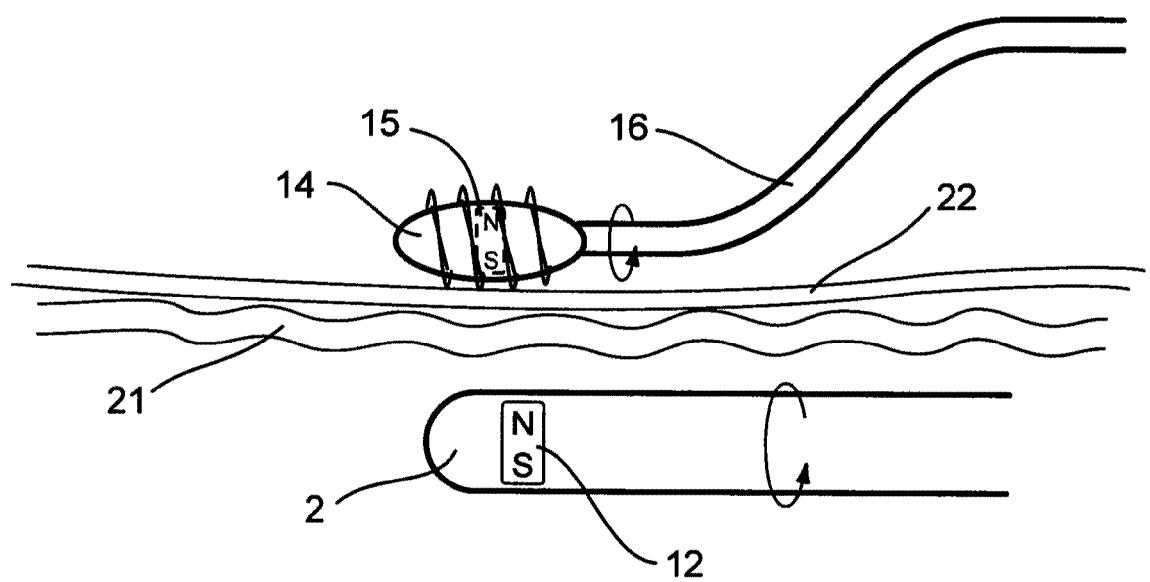
FIG. 16 shows another further embodiment of the distal tip of the ablating member.

FIG. 16 shows another alternate embodiment of the ablating tip 14, in which the ablating tip is shaped as an ovoid volume and further comprises an helically shaped ridge on its periphery. The purpose of this helically shaped ridge is to improve the displacement of the ablating tip 14 by minimizing the contact zone between the tissues and the tip. Thanks to this helically shaped ridge, the ablating tip is free to rotate on itself when moving along the atrial surface. In these embodiments, the plastic tube 16 will preferably be made in material that is more soft and flexible that the material used for the tube 3 of the guiding member, this to minimize the resistance and to improve the guiding of the ablating tip.

Figure 17:
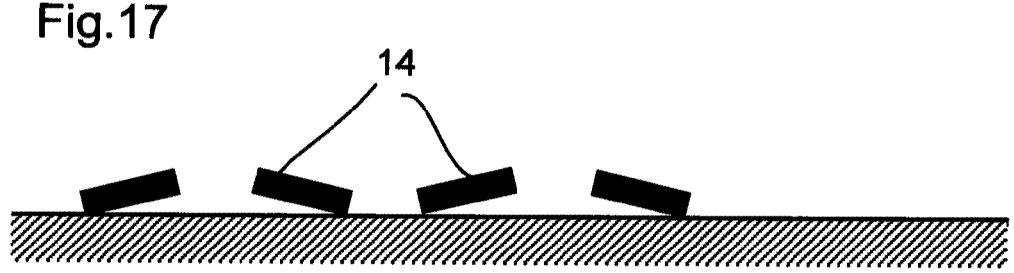
FIG. 17 is a schematic side view illustrating the displacement of the ablating tip.
Figure 18:
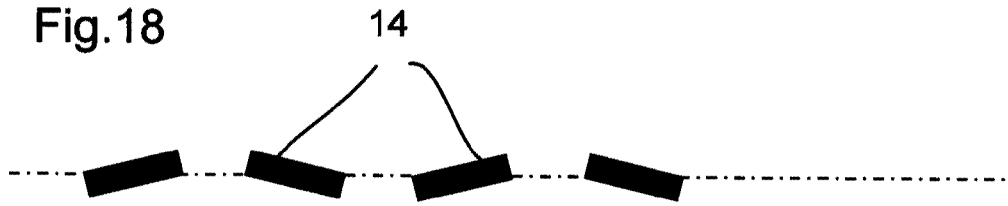
FIG. 18 is a schematic top view illustrating the displacement of the ablating tip.

Referring to FIGS. 17 and 18, which are respectively a side view and a top view of the schematically represented ablating tip moving along the tissue surface, one sees that thanks to the movement (either rotational or back and forth) applied on the guiding member, the ablating tip slowly rotates and is axially shifted at the same time thus rendering the progression easier of the ablating tip on the wall of the atrium especially in presence of obstacles. The back and forth and/or rotational movement can be achieved manually by the surgeon when performing the intervention but preferably, the guiding member is arranged with mechanical means (pneumatic or electric motor) to achieve the back and forth or rotational movement of the head 2 of the guiding member.

Figure 19:
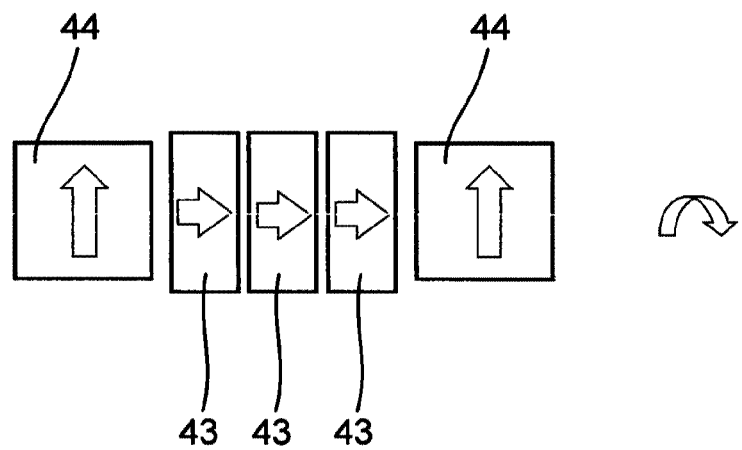
FIG. 19 shows a magnet arrangement intended to be installed in the head of the guiding member.

While a single magnet 12 is depicted in the distal head of the guiding member 2, at FIGS. 14, 1 and 16, it may obviously be replaced by a magnet arrangement. An example of such a magnet arrangement is depicted at FIG. 19 which shows 3 central magnets 43 longitudinally located in the head of the guiding member and two vertically arranged magnets 44. All these magnets are magnetized axially (with respect to the magnet). A single magnet can obviously replace the central portion constituted of three magnets. This magnet configuration is similar to a Hallbach array, but due to another orientation of end magnets, an asymmetric magnetic field is created in this case.

Figure 20:
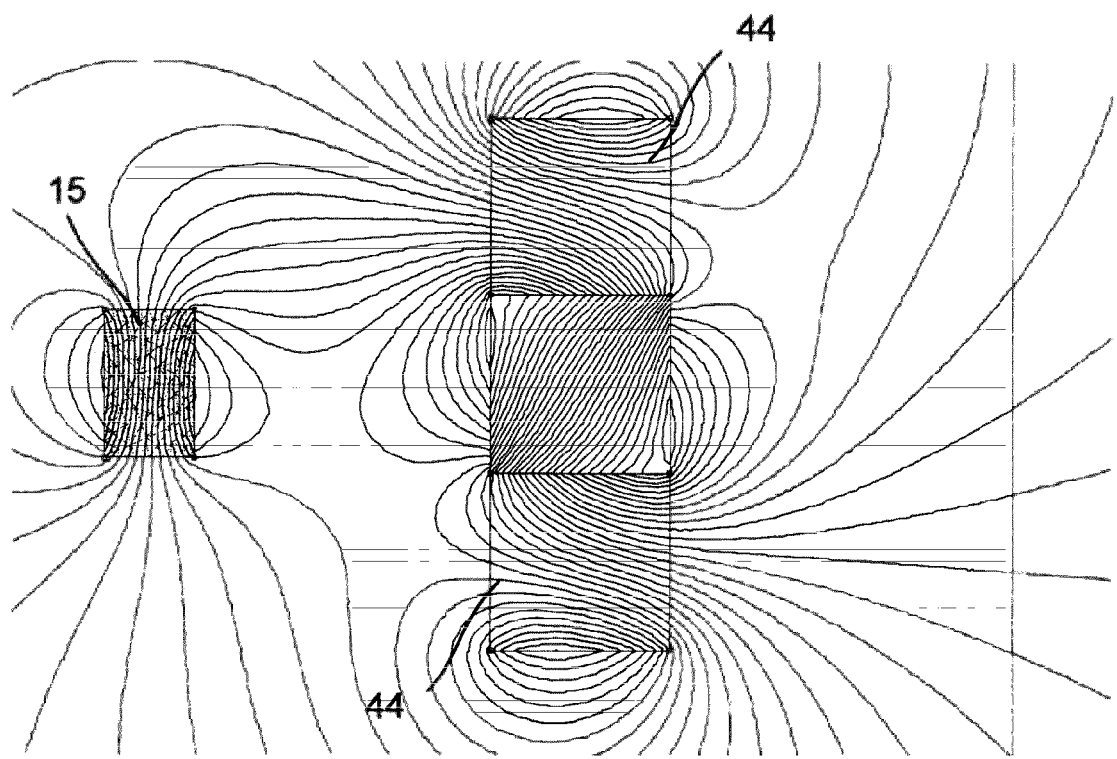
FIG. 20 illustrate the magnetic field generated by the magnet arrangement of FIG. 19.

FIG. 20 shows schematically the magnetic field generated by this magnet arrangement.

Figure 21:
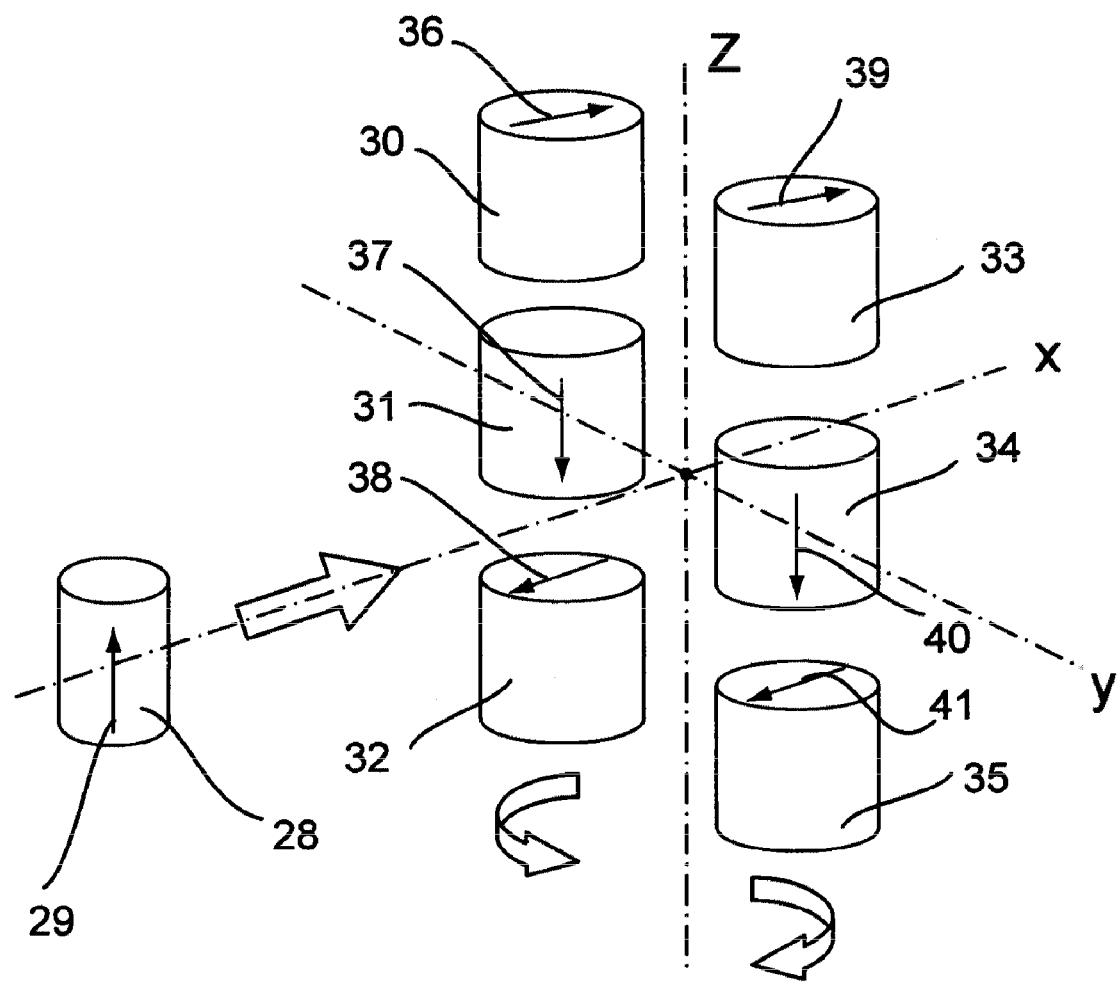
FIG. 21 is a schematic view of a magnet arrangement used in the guiding member of the medical device.
Figure 22:
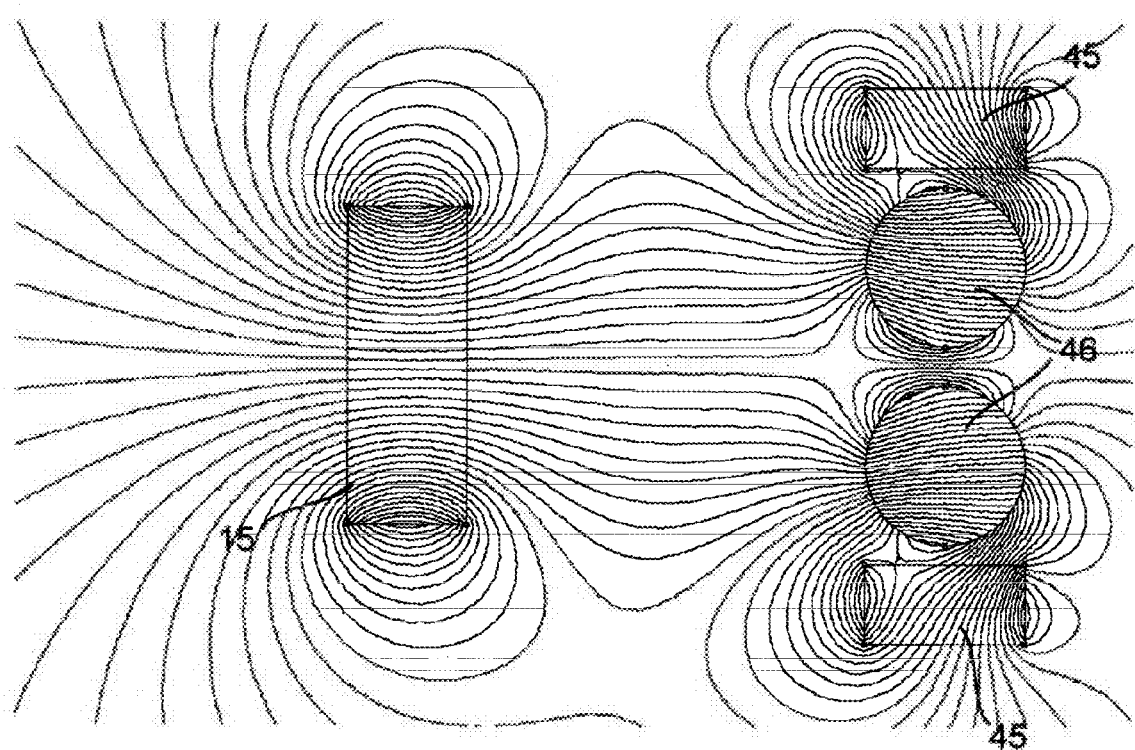
FIG. 22 is an alternate magnet arrangement used in the guiding member.

While the magnetised portion of the head 2 of the guiding member has been described until now with reference to a single permanent magnet at FIGS. 2 to 13, it can also be substituted by a specific magnets arrangement. Such an arrangement is depicted schematically at FIG. 21. On the left side of said figure, the magnet located within the ablating tip 21 is represented as a cylindrical magnet 28 positioned at a certain distance of from the origin of the y-axis. The arrow 29 represents the magnetization orientation of said magnet. The magnet arrangement that is intended to be inserted in the head 2 of the guiding member is depicted on the right side of picture 21. This magnet arrangement is composed of two groups of three different permanent magnets 30,31,32,33, 34,3 located symmetrically with regard to the z-axis. The corresponding arrows 36,37,38,39,40,41 indicate their respective magnetisation orientation. In order to control the magnitude of the magnetic force between the magnet 28 and the magnet arrangement 30,31,32,33,34,3, the magnets 30,31,32,33,34,3 will be synchronously rotated. If the left column of magnets (30,31,32) is rotated in the counter-clockwise direction then the right column of magnets (33,34,3) has to be rotated in the clockwise direction or vice versa by the same angle. By this rotation of the magnets, the force of attraction between the magnet 28 and the arrangement of magnets in the head of the guiding member can be decreased down to zero or even transformed to a repulsive force if needed. The force magnitude depends both on the distance and the rotation angle. It is therefore possible with such an arrangement to vary the attraction force between the ablating tip 14 and the head 2 of the guiding member located in the oesophagus. The position of the magnets arrangement shown at FIG. 14 corresponds to the maximum force exerted on the magnet 28. Obviously, other arrangements with different configurations of rotating magnets are possible to achieve the same result. An example of an alternate configuration is depicted at FIG. 22 which show a magnet arrangement composed of two cylindrical magnets surrounded by two cuboids magnets 46.

With the combination of the pressure/force sensor and the adjustable magnetic force, the clinician can precisely adapt the force of attraction between the guiding member and the ablating tip.

Thanks to the magnetic coupling of the ablating tip 14 with the head 2 of the guiding member, the position of the ablating electrode is determined and always perpendicular to the tissue to ablate and therefore continuous ablation lines can be achieved. With the temperature sensor located in the head 2 of the member not bearing the ablation electrode, the clinician has a precise knowledge of the physiological condition in the vicinity of the ablation area and therefore energy delivered to the ablation electrode can be adjusted and optimised so as to prevent burning of the oesophageal wall during the intervention.

The working principle of this medical apparatus will now briefly be described. The main purpose of this device is to produce continuous ablation line on the left atrium wall thanks to the energy delivered to the ablating electrode located in the tip 14 of the ablation member. Once the cardiac mapping has been executed so as to precisely determine the ablation lines or zones to be treated in the atria, the ablation catheter is introduced through natural passageway, vein or artery usually in the groin or neck area, and further guided by the physician into the chosen heart chamber by appropriate manipulations of the steering mechanism. Once the ablation catheter is in place in the atrium, the guiding member or oesophageal catheter is introduced through the mouth or the nose of the patient into its oesophagus until the head 2 of the guiding member reaches the vicinity of the left atrium. It may be noted that other introduction sites are also possible to achieve the same result.

Once this position is reached, the head 2 of the oesophageal catheter will enter in magnetic coupling with the tip 14 of the ablation catheter. Magnetic coupling of the tip 14 and the head 2 occurs trough both the oesophageal wall and the left atrial wall. Once the head 2 and the ablation tip 14 are connected, the ablation catheter tip 14 may be controlled and guided by moving only the oesophageal catheter both longitudinally by pulling and pushing the oesophageal catheter as well as laterally by acting on the command buttons, 6 which will cause a flexion of the distal end of the oesophageal catheter head 2. Therefore, the ablation tip of the ablation catheter can be moved within the left atrium chamber by acting only on the oesophageal catheter, without the need of acting on the steering mechanism of the member bearing the ablation electrode. The movements of the oesophageal catheter will drag down the magnetically coupled ablation tip 14 allowing controlled displacement of the ablation tip along the inner surface of the left atrium. These steps are generally performed under fluoroscopy or any other suitable non-invasive imaging technique to assist the clinician to correctly position the two catheters and to allow the magnetic coupling of the head 2 and the ablation tip 14. Once the catheters are in place and magnetically coupled, the trajectory of the ablation lines is defined and a first movement run is performed without applying RF energy to the ablation tip. The longitudinal movements of the system across the left atrium are performed by pulling, respectively pushing the oesophageal catheter. The amplitude of the longitudinal movement is measured with reference to the markers appearing on the section of the proximal end of the oesophageal catheter. The perpendicular movements are achieved thanks to lateral flexion of the oesophageal catheter obtained by actuating the steering mechanism of the guiding member. Thanks to the rotating ball or the signal delivered by the optical fibres shown at FIGS. 12 and 13, the displacement of the ablating tip 14 can be precisely monitored and calculated.

Subsequently, a second run is performed where the systems stops about every 3 to 4 millimetres and energy is applied thanks to a generator to the ablation electrode in order to produce lesions of approximately 4 millimetres in diameter. This results in the production of a continuous ablation line along the overall determined trajectory.

Alternatively the ablation tip 14 may be equipped with other ablating means known in the art, such as laser ablation, cryogenic ablation, ultrasound ablation, micro-waives ablation, others.

Advantageously position sensors known in the art could be integrated into the tip 14 of the ablation catheter and/or the head 2 of the guiding member to provide direct 3D position coordinates of both catheters.

In a simplified embodiment, only one of the two members of the medical device may be equipped with means for moving its distal end. For example, the member bearing the ablating tip can be constituted of a simple flexible tube with a distal end comprising the ablation electrode as well as the magnet. This member is introduced for example within the upper chamber of the heart with a guide catheter and pushed through the sheath of the catheter. Alternatively, the member bearing the temperature sensor may also be constituted of a single flexible body having at its distal end a head comprising a magnet and a temperature sensor. In that case, after magnetic coupling with the member bearing the ablation electrode, the guiding of the ablating member is realized with traditional means used in catheter intervention as disclosed in the previous paragraphs.

While this technique has been disclosed in relation to the left atrial treatment, it is clear that in practice, the same principle could be applied to ablate other regions of the heart like the atrial septum. In that case the catheter bearing the temperature sensor will be placed in the right atrium and the ablation catheter in the left atrium. If the lower-posterior part of the atria is to be ablated, the member bearing the temperature sensor will be placed into the coronary sinus and the ablation catheter into the left or right atrium. Should the left ventricle be ablated the member bearing the temperature sensor will be positioned into coronary vein and the ablating catheter into the left ventricle. Other locations are also possible. The working principle remains the same; only the size and configuration of the members should be adapted to be introduced in the above referenced regions of the human body.

Thanks to this medical device, and method, a complete control over the ablating tip is achieved and allows the generation of precise continuous lines of ablation in the region to be treated, while minimizing the risk of thermal injury to the regions to be treated thanks to a precise measure of the temperature of the tissues in the vicinity of the region to be treated.

While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

The invention claimed is:

1. Medical device for performing tissue ablation in a heart chamber characterized in that it comprises a guiding member intended to be introduced by natural passageways in a first region of the human body, said guiding member having a distal end comprising a head incorporating at least one magnet as well as a temperature sensor; the medical device further comprising an ablating member intended to be introduced in a heart chamber having a distal ablation tip comprising at least one ablating means as well as at least one magnet, wherein magnetic coupling is adapted to occur through human tissue between the at least one magnet of the guiding member and the at least one magnet of the ablating member and the guiding member controls of the alignment of the ablating member to ablate tissue at a discrete location and guides the movement of the ablation tip along a predetermined trajectory to ablate tissue along said trajectory.

2. Medical device according to claim 1, wherein at least one of the members comprises a proximal end and at least one lumen extending between the proximal and the distal ends as well as a steering mechanism actuated by a handle for moving the distal head.

3. Medical device according to claim 1, wherein the guiding member is configured to be introduced in the esophagus of the patient and the ablating member bearing the ablation tip in the left atrium of the heart.

4. Medical device according to claim 1, wherein the head of the guiding member is shaped to present at least a flat surface intended to be in contact with the inner wall of the esophagus.

5. Medical device according to claim 1, where the head of the guiding member comprises a recess adapted to dock the distal ablation tip of the ablating member.

6. Medical device according to claim 1, wherein the head of the guiding member, at its side adapted to be in contact with tissue, further comprises a sensor located in the vicinity of the temperature sensor for measuring the force created on the tissue between the at least one magnet of the guiding member and the at least one magnet of the ablating member.

7. Medical device according to claim 1, wherein the head of the guiding member comprises an arrangement of movable magnets arranged in such a way that the amplitude of the magnetic attraction force between the head and the tip of the ablating member can be adjusted and controlled.

8. Medical device according to claim 1, wherein the ablation tip comprises a spherical recess and a ball free to rotate inside the recess and means for measuring the displacement of the ball and, hence, the displacement of the ablation tip.

9. Medical device according to claim 1, wherein the guiding member comprises means for inducing a back and forth or a rotational movement of the head.

10. Medical device according to claim 1, wherein the head of the ablation tip presents an ovoid shape.

11. Medical device according to claim 10, wherein the ablation tip comprises a helically shaped ridge on its periphery.

12. The medical device according to claim 1, further comprising means for measuring the force produced by the displacement of the at least one magnet of the guiding member relative to the at least one magnet of the ablation member while the distal ablation tip moves along a length of tissue.

13. A method of guiding the tip of an ablating member during cardiac tissue ablation in a heart chamber comprising the following steps:
inserting and placing the tip of an ablating member mounted at the distal end of a catheter into a heart chamber;
inserting the distal head of a guiding member into the esophagus of the patient or other location in the vicinity of the heart chamber to be treated;
having the head of the guiding member and the tip of the ablating member entering into magnetic coupling;
positioning the tip of the ablating member at a first location using the guiding member;
applying energy to the tip of the ablating member to perform cardiac tissue ablation at the first location;
guiding the tip of the ablating member along a predetermined trajectory at least to a second location by moving only the guiding member.

14. The method of claim 13, further comprising the step of monitoring the temperature of the tissue with a temperature sensor mounted at the head of the guiding member and adapting the energy delivered to the tip of the ablating member according to the temperature measured.

15. The method of claim 13, further comprising the step of monitoring the attraction force between the tip of the ablating member and the head of the guiding member.

16. The method of claim 13, further comprising the measuring of the displacement of the tip of the ablating member.

17. The method of claim 13, further comprising applying a movement either rotational or back and forth to the head of the guiding member.

18. The method of claim 13, further comprising sensing the position of the ablating member relative to the guiding member by measuring the strength of the magnetic coupling while the tip of the ablating member moves along a length of tissue.

* * * * *

UNITED STATES PATENT AND TRADEMARK OFFICE
CERTIFICATE OF CORRECTION

PATENT NO. : 8,048,072 B2
APPLICATION NO. : 12/373281
DATED : November 1, 2011
INVENTOR(S) : Vitali Verin and Jan Sandtner Page 1 of 1

It is certified that error appears in the above-identified patent and that said Letters Patent is hereby corrected as shown below:

Title page, item [73] Assignee should read:   Les Hôpitaux Universitaires de Genève Signed and Sealed this
Twenty-sixth Day of February, 2013

Teresa Stanek Rea
*Acting Director of the United States Patent and Trademark Office*